United States Patent [19]

Auweter et al.

[11] Patent Number: 4,637,716
[45] Date of Patent: Jan. 20, 1987

[54] FIBER-OPTICAL DOPPLER ANEMOMETER

[75] Inventors: Helmut Auweter, Ludwigshafen; Dieter Horn, Heidelberg; Erik Lueddecke, Mutterstadt, all of Fed. Rep. of Germany

[73] Assignee: BASF Aktiengesellschaft, Fed. Rep. of Germany

[21] Appl. No.: 533,866

[22] Filed: Sep. 20, 1983

[30] Foreign Application Priority Data

Sep. 24, 1982 [DE] Fed. Rep. of Germany ....... 3235369

[51] Int. Cl.$^4$ ............. G01P 3/36; G01N 21/00; G01B 9/02; G02B 6/26
[52] U.S. Cl. ................. 356/28.5; 356/337; 356/349; 350/96.15
[58] Field of Search ............ 356/28, 28.5, 5, 335, 356/336, 337, 350, 349; 350/96.15

[56] References Cited

U.S. PATENT DOCUMENTS 4,154,529 5/1979 Dyott .................. 356/28.5

FOREIGN PATENT DOCUMENTS 57-79472 5/1982 Japan ................... 356/337
2076960 5/1980 United Kingdom .

OTHER PUBLICATIONS

Applied Optics, 14 (1975), 189.
Microwaves, Optics and Acoustics, 2 (1978), 13.
Nishihara et al, "Optical-Fiber Laser Doppler Velocimeter for High-Resolution Measurement of Pulsatile Blood Flows," from *Applied Optics*, 15 May 82, pp. 1785-1790.
Ross et al, "The Determination of the Mean and Standard Deviation of the Size Distribution of a Colloidal Suspension of Submicron Particles Using the Fiber Optic Doppler Anemometer, FODA, *Journal of Colloid and Interface Science*, May, '78, pp. 533-542.

*Primary Examiner*—Stephen C. Buczinski
*Assistant Examiner*—Linda J. Wallace
*Attorney, Agent, or Firm*—Keil & Weinkauf

[57] ABSTRACT

In a fiber-optical Doppler anemometer for measurement of fluctuating light or the Doppler broadening of laser light scattered by a scattering medium, for example by particles in motion, coherent laser light is passed via a fiber-optical coupler (1) and a submerged fiber-optical probe (2) into the scattering medium, and the light scattered back by the scattering medium is picked up by the submerged fiber-optical probe (2), branched by the fiber-optical coupler (1) and passed to a photodetector (3).

6 Claims, 4 Drawing Figures

FIBER-OPTICAL DOPPLER ANEMOMETER

The present invention relates to a fiber-optical Doppler anemometer for measuring fluctuating light or the Doppler broadening of laser light scattered by a scattering medium, for example by particles in motion.

A fiber-optical Doppler anemometer can be used for two basically different purposes. On the one hand, it can be employed in velocimetry, where it is possible to measure flow rates, velocity gradients and turbulence even at remote points which are inaccessible to a direct laser beam. Examples include the streams in metal pipes, in combustion engines and in blood vessels.

On the other hand, the fiber-optical Doppler anemometer can be used in physicochemical analysis to determine diffusion coefficients and the diameters of dispersed colloidal particles using photon-correlation spectroscopy. The said anemometer makes it possible to carry out these measurements in situ, in particular at points which are not readily accessible, for example in reaction vessels or in areas where there is a risk of explosion. Moreover, it can be used to examine highly concentrated and absorbing samples. As a result of these properties, the fiber-optical Doppler anemometer appears to be useful in monitoring and controlling production processes.

The principle of the fiber-optical Doppler anemometer is based on the Doppler shift of light which has been scattered by moving particles. Where the anemometer is used in velocimetry the particle motion is due to a flow. On the other hand, where the anemometer is used for determining diffusion coefficients and particle diameters, the particle motion is due to Brownian molecular motion.

It is known that a fiber-optical Doppler anemometer has been realized technically, and this is described in the literature (Applied Optics 14 (1975), 189). A feature of the construction of this apparatus is the fact that the laser light is guided, via a beam divider, to a submerged fiber-optical probe. Some of the light scattered back by the scattering medium is reflected to a photodetector by the same beam divider. In this manner, 75% of more of the available light intensity is lost.

This loss of intensity can be reduced by replacing the beam divider by a fully reflecting mirror with a hole bored through its center (Microwaves, Optics and Acoustics 2 (1978), 13). The laser light passes, without loss of intensity, through this hole in the mirror and is focused onto a submerged fiber-optical probe. The light which is scattered back by the scattering medium leaves the probe and is then collimated, at the angle determined by the numerical aperture of the light guide, by the focusing lens, and illuminates a relatively large area of the mirror. Hence, a high percentage of the scattered light is reflected onto the photodetector. Depending on the dimensions, the losses are only 5-10% of the light intensity.

In the fiber-optical Doppler anemometer the Doppler shift of the scattered light is measured quantitatively by heterodyne detection, since the photodetector registers an overlap of scattered, Doppler-shifted light with non-shifted laser light. The non-shifted laser light originates from reflections at the ends of the submerged fiber-optical probe and from Rayleigh scattering at the molecules of the light guide. The heterodyne fluctuation signal is recorded electronically either by frequency analysis or by autocorrelation analysis. The flow rate and the diffusion coefficient can be determined from the curve of the measured frequency distribution or autocorrelation function respectively. For monodisperse, spherical and non-interacting particles, for example, the relationship between the decay constant of the autocorrelation function, $\Gamma$ (which is identical to the half-width of the Lorentz frequency distribution), and the diffusion coefficient D is given by $$\Gamma = DK^2,$$

where K is the scattering vector.

In evaluating the measurements, it should be noted that the fiber-optical Doppler anemometer employs a 180° scattering geometry. This means that, for a polydisperse sample, the mean diffusion coefficient measured is of the form $$\overline{D}_{180°} = \frac{\Sigma_i N_i M_i^2 P(180°, M_i) D_i}{\Sigma_i N_i M_i^2 P(180°, M_i)}$$

where $N_i$ is the number, $M_i$ is the mass, $D_i$ is the diffusion coefficient and $P(180°, M_i)$ is the scattering function of the particles of the i-th component of the polydisperse distribution. From this expression, using the Stokes-Einstein relationship $$\overline{d}_{180°} = \frac{kT}{3\pi\eta \overline{D}_{180°}}$$

it is possible to calculate the associated hydrodynamic spherical particle diameter $d_{180°}$. In this expression, k is the Boltzmann constant, T is the temperature and $\eta$ is the viscosity of the solvent.

Previous forms of the fiber-optical Doppler anemometer are constructed using individual optical modules and, in addition to a beam divider or apertured mirror, require a number of other optical components, eg. polarizers, lenses and iris stops, as well as precision mountings for the laser and the light guide. Because of the heterodyne detection method employed, the entire optical arrangement must possess stability of interferometric quality. An arrangement of this type is very expensive and requires a substantial amount of space. Due to these factors, the previous technical forms of the fiber-optical Doppler anemometer are suitable only for laboratory use.

It is an object of the present invention substantially to simplify the construction of the fiber-optical Doppler anemometer and at the same time to increase its flexibility in order to extend the range of possible uses.

We have found that this object is achieved, in accordance with the invention, by a method in which coherent laser light is passed via a fiber-optical coupler and a submerged fiber-optical probe into the scattering medium, and the light scattered back by the scattering medium is picked up by the submerged fiber-optical probe, branched by the fiber-optical coupler and passed to a photodetector.

In accordance with the invention, the construction of the fiber-optical Doppler anemometer is further simplified and improved if the laser used is an integrated semiconductor laser and the laser light is passed directly via a light guide to the fiber-optical coupler, the photodetector used is an integrated detector, eg. a silicon avalanche photodiode, and the scattered light branched off by the fiber-optical coupler is passed directly via a light guide to the detector, the anemometer construction is completely integrated, and the submerged fiber-optical probe consists of a light guide which is terminated by a sleeve and is furthermore surrounded by a protective tube and also rendered hydrophobic at one end.

Using the novel fiber-optical Doppler anemometer, it is possible to measure flow rates of fluid and gaseous media, particularly in blood vessels, to measure diffusion coefficients and particle diameters of colloidal systems, to add particles of known size to the medium under investigation and to calculate the viscosity of the medium from the measured diffusion coefficient. The particular advantage obtained by means of the invention is that, instead of being constructed from individual, precisely mounted optical components, the anemometer can have a partially or completely integrated construction so that the path of the laser light and of the scattered light runs mainly or completely through light guides and fiber-optical components. As a result, all individual optical components can be dispensed with and the construction need not possess stability of interferometric quality.

The arrangement can be operated anywhere since it is no longer necessary to assemble it on an optical bench. The fiber-optical components are merely connected together by appropriate plug connections. Moreover, it is possible to carry out the measurement at inaccessible points since the submerged fiber-optical probe is flexible and can be of considerable length.

The use of fiber-optical components conventionally employed in communications technology makes the fiber-optical Doppler anemometer very easy to handle. This opens up many new possible applications in velocimetry and in the measurement of diffusion coefficients in research and industry.

Two examples of the invention are illustrated and described below.

Figure 1:
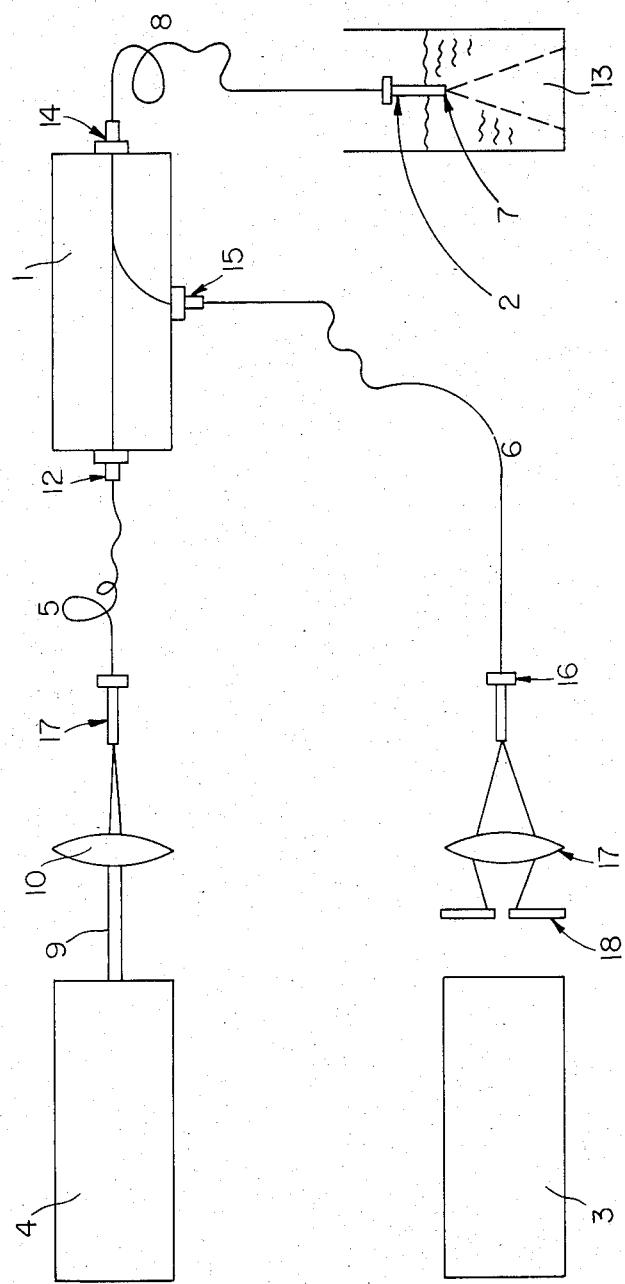
FIG. 1 shows a fiber-optical Doppler anemometer using a fiber-optical coupler.

Using a fiber-optical coupler 1, a laser beam 9 emerging from a laser 4 is focused, with the aid of a lens 10, onto the light guide 5 which is terminated by a sleeve 11. This light guide 5 is connected to the coupler 1 via a plug connection 12. The laser light re-emerges from the coupler 1 and is passed into a sample 13 via a light guide 8. This light guide 8 is terminated by a sleeve 7 and constitutes the submerged fiber-optical probe 2. The laser light emerges at the end of the light guide at an angle $\alpha = 2 \arcsin (NA)$, where NA is the numerical aperture of the light guide.

The light scattered back by the sample 13 once again enters the light guide 8 via the terminal sleeve 7 and passes to a plug connection 15 via a plug connection 14 of the coupler 1. The fluctuating scattered light is passed, via a light guide 6, to a detector 3, which it reaches after it has emerged from a terminal sleeve 16, been focused by a lens 17 and been limited by a pinhole 18.

Figure 2:
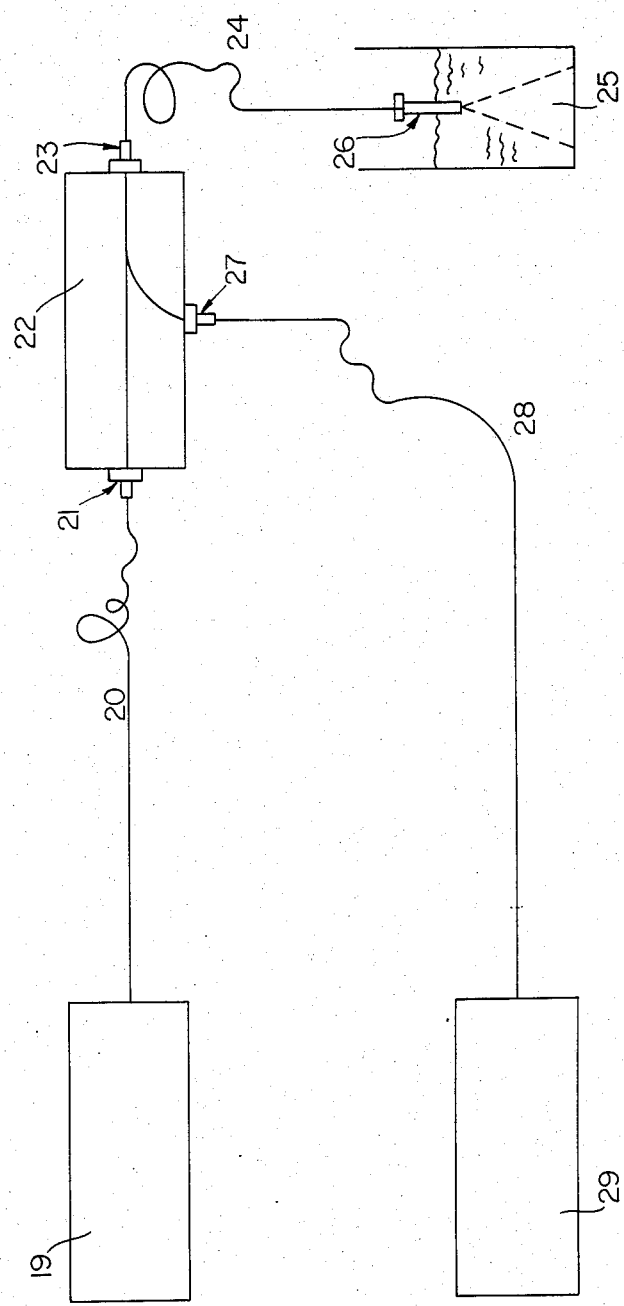
FIG. 2 shows a fully integrated version of a fiber-optical Doppler anemometer.

In the arrangement shown in FIG. 2, coherent laser light passes directly from a semi-conductor laser 19, via a light guide 20, to a plug connection 21 of a coupler 22. The laser light re-emerges at a plug connection 23 and passes via a light guide 24 into a sample 25, where it emerges from the light guide 24 which is terminated by a sleeve 26.

The light scattered back by the sample 25 passes via the light guide 24 and the plug connection 23 to a plug connection 27 and from there directly via a light guide 28 to a photodetector 29. In this embodiment, the entire path of the scattered light runs in light guides or in fiber-optical components.

Figure 3:
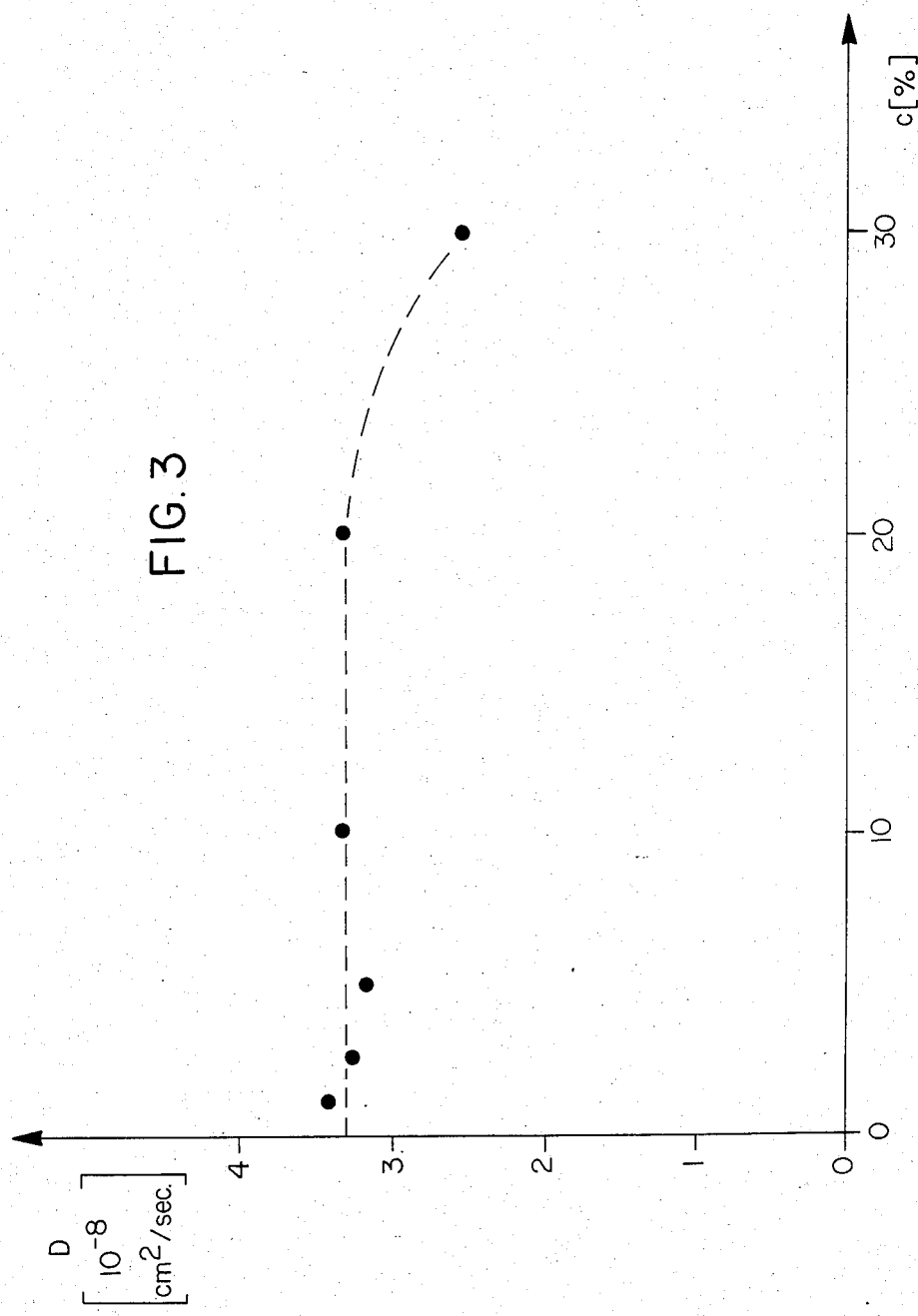
FIG. 3 shows the diffusion coefficient of a latex dispersion as a function of the solids concentration.

FIG. 3 shows a typical result of a measurement of the diffusion coefficient D of a latex dispersion as a function of the solids concentration. At concentrations higher than 20%, the diffusion coefficient becomes smaller since the viscosity of the dispersion increases.

Figure 4:
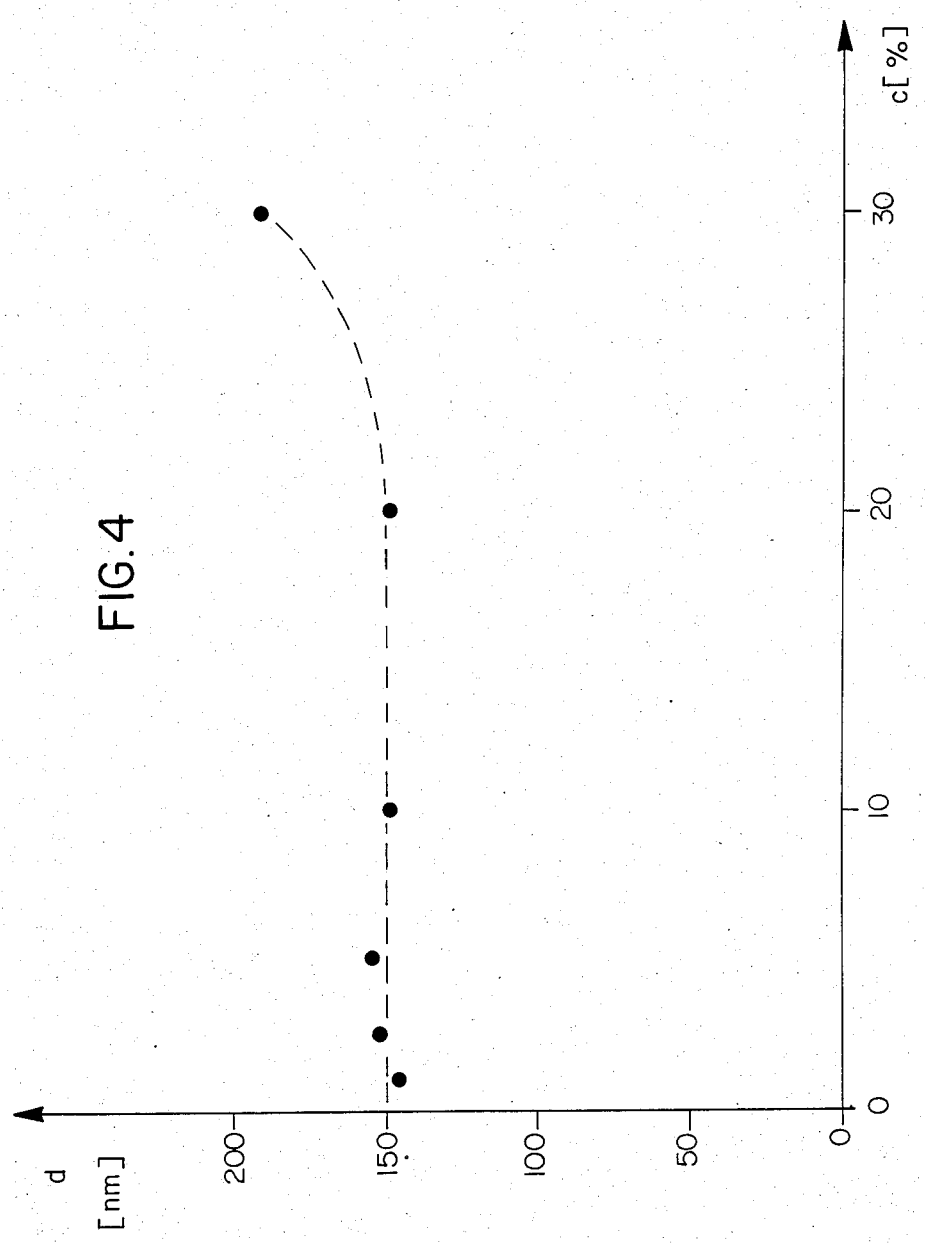
FIG. 4 shows the spherical hydrodynamic particle diameter of latex particles as a function of the solids concentration.

FIG. 4 shows the spherical particle diameter, likewise as a function of the solids concentration, calculated from the diffusion coefficient using the Stokes-Einstein relationship. At concentrations higher than 20%, deviations from the true particle diameter appear since the free diffusion of the particles is hindered because of the high concentration.

We claim:

1. A fiber-optical Doppler anemometer for measuring the Doppler broadening of laser light passing through a scattering medium containing moving particles, which anemometer comprises:
  (a) a laser light emitting means;
  (b) a fiber-optical coupler arranged to receive the laser light from the emitting means;
  (c) a fiber optical probe submerged in the scattering medium and arranged
    ($c_1$) to receive the light from the fiber-optical coupler, and
    ($c_2$) to return the light scattered by the moving particles to the fiber-optical coupler along with non-shifted light, said non-shifted light being coherent with the scattered light; and
  (d) a photodetector device arranged to receive a beam of light split in said fiber-optical coupler, said light including both light scattered by the moving particles and light otherwise returned to the fiber-optical coupler, said photodetector serving to compare the frequencies of the light scattered by he moving particles and the light otherwise returned to the coupler from the optical probe.

2. A fiber-optical Doppler anemometer according to claim 1, wherein the laser light emitting means is an integrated semiconductor laser and the laser light is passed directly via a light guide to the fiber-optical coupler.

3. A fiber-optical Doppler anemometer according to claim 1, wherein the photodetector is an integrated detector and the scattered light branched off by the fiber-optical coupler is passed directly via a light guide to the detector.

4. A fiber-optical Doppler anemometer according to claim 1, wherein the anemometer construction is completely integrated.

5. A fiber-optical Doppler anemometer according to claim 1, wherein the submerged fiber-optical comprises a light guide which is terminated by a sleeve surrounded by a protective tube and rendered hydrophobic at its end.

6. A method of measuring the Doppler broadening of laser light scattered by contact with moving particles in a scattering medium which comprises:

passing a beam of laser light through a fiber-optical coupler and then through a fiber-optical probe arranged in sequence with said coupler, said probe being submerged in the scattering means, whereby a portion of the light is scattered by the moving particles;

returning the light scattered by the particles to the coupler via the fiber-optical probe along with non-shifted laser light, whereby said light is branched by the coupler and passed to a photodetector whereby the frequencies of the scattered light and non-shifted light are compared.

* * * * *